United States Patent [19]
Ford, Jr.

[11] Patent Number: 5,305,073
[45] Date of Patent: Apr. 19, 1994

[54] METHODS AND APPARATUS FOR MOLECULAR CHARACTERIZATION

[75] Inventor: Norman C. Ford, Jr., Amherst, Mass.

[73] Assignee: Precision Detectors, Inc., Amherst, Mass.

[21] Appl. No.: 834,415

[22] Filed: Feb. 12, 1992

[51] Int. Cl.$^5$ .............................. G01N 15/06
[52] U.S. Cl. ...................... 356/338; 356/339
[58] Field of Search ............... 356/338, 339

[56] References Cited

U.S. PATENT DOCUMENTS

| | | | |
|---|---|---|---|
| 2,427,996 | 9/1947 | Seaman | 356/130 |
| 4,027,973 | 6/1977 | Kaye | 356/338 |
| 4,053,229 | 10/1977 | McCluney | 356/338 |
| 4,804,853 | 2/1989 | Borden et al. | 356/338 |
| 4,948,260 | 8/1990 | Felix et al. | 356/429 |
| 5,017,008 | 5/1991 | Akiyama | 356/338 |

OTHER PUBLICATIONS

Korableva et al. "Installation for the Measurement of Scattering and Depolarization of Light by a Liquid". *Instruments and Experimental Techniques* vol. 21, No. 4, Pt. 2 (Jul.-Aug. 1978) pp. 1088-1089.

Berrue et al "A New Apparatus for Measuring the Depolarization Ratio of Light Scattered by Gaseous Argon, Methane and Tetrafluoromethane" *Optics Communications*, vol. 31, No. 3 (Dec. 1979) pp. 317-320.

"dp-801 TM Molecular Size Detector", Biotage, Inc. brochure, 1991, (two pages).

"CMX-100 Light Scattering Detector", LDC/Milton Roy brochure, 1983, (6 pages).

"The KMX-6-A Unique Molecular Weight Detector in Size Exclusion Chromatography", LDC/Milton Roy Broc., 1983, (7 pages).

"Dawn® . . . Macromolecular Characterization by Multi-Angle Laser Light Scattering", Wyatt Technology brochure, 1990, (8 pages).

"Right Angle Laser Light Scattering Detector", Viscotek brochure date unknown, (2 pages).

*Primary Examiner*—Richard A. Rosenberger
*Attorney, Agent, or Firm*—Wolf, Greenfield & Sacks

[57] ABSTRACT

A molecular characterization detector includes a scattering cell containing a sample for molecular characterization, a light source for directing a light beam through the cell so that the light beam is scattered by the sample, optical elements for selecting from the scattered light a measurement beam comprising light that is scattered by the sample from a predetermined portion of the cell in a predetermined range of angles relative to the optical axis, and a detector for detecting the measurement beam and providing an output electrical signal representative of the measurement beam. The detector typically selects light scattered from a central portion of the scattering cell at angles in the range of 14° to 16°. A single spherical lens is preferably utilized. As a result, interference from stray scattered light is minimized. A beam dump attenuates the light beam after it passes through the scattering cell. Additional detectors detect light scattered at 90° to the light beam. The outputs of the detectors are processed to provide molecular characterization of the sample.

26 Claims, 8 Drawing Sheets

METHODS AND APPARATUS FOR MOLECULAR CHARACTERIZATION

FIELD OF THE INVENTION

This invention relates to methods and apparatus for molecular characterization and, more particularly, to a molecular characterization instrument wherein light is scattered by molecules of a sample, and the scattered light is detected and analyzed. The molecular characterization instrument is typically utilized with a liquid chromatography system, but is not limited to such use.

BACKGROUND OF THE INVENTION

A well known need exists within industries involved with macromolecules to characterize molecules created by or used in various processes. Application areas where this need is of particular interest include quality control laboratories, research laboratories and manufacturing operations in the plastics, pharmaceutical, biotech and chemicals industries. Typical measurements to characterize molecules include determination of the molecular weight distributions and polydispersity when different molecular weights are included in the sample, molecular sizes (hydrodynamic radii, radii of gyration), concentrations and conformation information, including shape information and molecular branching information.

The most common technique for molecular characterization is liquid chromatography (LC), which involves the preparation of the sample for the particular detection method to be used and the detection method itself. In this well known analytical technique, a flowing mixture of a solvent and the substances to be tested (a mixture of molecules with various molecular weights and other molecular characteristics) is passed through specifically selected chromatography columns which result in the component molecules being separated in time in the flowing solvent according to their size or according to some other molecular characteristic. The flowing fluid then passes through the detector. In one type of detector, a laser beam is directed through the fluid, and the scattered light is analyzed to provide molecular characterization.

Examples of uses of liquid chromatography are the analyses of proteins, commercial resins, natural and synthetic polymers, neucleic acids, plasticizers, plant and animal metabolites, lubricants, dyes, petroleum residues, pharmaceuticals, amino acids, pigments, polysaccharides, pesticides, herbicides, fungicides, surfactants, lipids, explosives, and other materials.

The detectors have used various techniques for detecting light scattered by sample molecules. In one prior art system, the sample is surrounded by an array of detectors which collect laser light scattered by the sample at different angles. In another prior art system, laser light scattered by the sample at a predetermined angle passes through an annular aperture and is focused on a photomultiplier. All of the known prior art molecular characterization detectors have had one or more disadvantages, including difficulty of use because of required optical alignment, low signal levels and interference from stray light, which reduces accuracy, and relatively high cost.

It is a general object of the present invention to provide improved methods and apparatus for molecular characterization.

It is another object of the present invention to provide a molecular characterization detector wherein interference from stray light is reduced in comparison with prior art detectors.

It is a further object of the present invention to provide improved molecular characterization instruments.

It is still another object of the present invention to provide a molecular characterization detector wherein light scattered by window surfaces is blocked from reaching the light detector.

It is yet another object of the present invention to provide a molecular characterization detector which is low in cost, easy to manufacture and which does not require optical alignment.

SUMMARY OF THE INVENTION

According to the present invention, these and other objects and advantages are achieved in methods and apparatus for molecular characterization. A molecular characterization detector in accordance with the invention comprises a scattering cell containing a sample for molecular characterization, means for directing a light beam through the cell so that the light beam is scattered by the sample, the light beam defining an optical axis, means for selecting from the scattered light a measurement beam comprising light from the light beam that is scattered by the sample from a predetermined portion of the scattering cell in a predetermined range of angles relative to the optical axis, and means for detecting the measurement beam and providing an output electrical signal representative of the measurement beam for characterization of the sample.

The means for selecting a measurement beam preferably comprises means for defining an annular aperture for passing the measurement beam and optical means for focusing light scattered by the sample on the annular aperture. The annular aperture is preferably defined by a first iris that blocks light scattered by the sample at angles greater than the predetermined range of angles and a second iris that blocks light scattered by the sample at angles less than the predetermined range of angles. In a preferred embodiment, the optical means comprises a lens which has a single spherical surface and which is an integral part of the output window of the scattering cell. In this case, the first iris and the second iris are axially spaced apart on the optical axis.

In the preferred embodiment utilizing a lens with a single spherical surface as described above, the means for selecting a measurement beam further comprises a third iris having a circular outside diameter centered on the optical axis and a fourth iris having a circular inside diameter centered on the optical axis. The third iris and the fourth iris select light that is scattered from a predetermined portion of the scattering cell. The predetermined portion of the scattering cell from which scattered light is selected is preferably a central region of the cell so that light scattered by the windows at the ends of the scattering cell is blocked from the measurement beam. The third iris and the fourth iris are located downstream of the annular aperture and are axially spaced apart.

The scattering cell preferably has a volume on the order of about ten microliters, and a liquid sample is continuously circulated through the scattering cell. A window is positioned on the optical axis at each end of the scattering cell to permit the light beam to pass through the sample. The light beam preferably comprises a polarized laser beam.

According to a another aspect of the invention, the molecular characterization detector preferably includes a beam dump for attenuating the light beam after it passes through the scattering cell. The beam dump preferably comprises an enclosure having an inlet for receiving the light beam and a generally cylindrical, light absorbing interior wall. A light-absorbing surface is located within the enclosure and is positioned for intercepting the light beam. The light-absorbing surface is oriented relative to the light beam at an angle that is selected to reflect the light beam to the interior wall of the enclosure. Preferably, the light-absorbing surface is formed on one end of an axially positioned, cylindrical post. The post and the interior wall of the enclosure define an annular space between them. The angle of the light-absorbing surface is selected to cause multiple reflections of the light beam in the annular space. The beam dump preferably includes means for guiding the light beam to the inlet of the enclosure, comprising a truncated conical surface having a first opening that is larger than the inlet for receiving the light beam and a second opening that defines the inlet of the enclosure.

According to a further aspect of the invention, there is provided a molecular characterization instrument comprising a scattering cell containing a sample for molecular characterization, means for directing a polarized light beam through the cell so that the light beam is scattered by the sample, the light beam defining an optical axis, means for detecting a first measurement beam comprising light from the light beam that is scattered by the sample in a predetermined range of angles relative to the optical axis and providing a first electrical signal representative of the first measurement beam for characterization of the sample, means for detecting a second measurement beam comprising light from the light beam that is scattered by the sample in a direction perpendicular to the light beam and perpendicular to the direction of polarization of the light beam and providing a second electrical signal representative of the second measurement beam for characterization of the sample, means for detecting a third measurement beam comprising light from the light beam that is scattered by the sample in a direction perpendicular to the light beam and parallel to the direction of polarization of the light beam and providing a third electrical signal representative of the third measurement beam for characterization of the sample, means for detecting a fourth measurement beam comprising fluctuations in light from the light beam that is scattered by the sample in a direction perpendicular to the light beam and providing a fourth electrical signal representative of the fourth measurement beam for characterization of the sample, means for determining the difference between the refractive index of the sample and a reference fluid by measuring a deviation angle of a light beam passing through a two chamber cell and providing a fifth electrical signal representative of the deviation angle for characterization of the sample, and means for processing the first, second, third, fourth and fifth electrical signals to provide a molecular characterization of the sample.

BRIEF DESCRIPTION OF THE DRAWINGS

For a better understanding of the present invention, together with other and further objects, advantages and capabilities thereof, reference is made to the accompanying drawings which are incorporated herein by reference and in which.

DETAILED DESCRIPTION OF THE INVENTION

Figure 1:
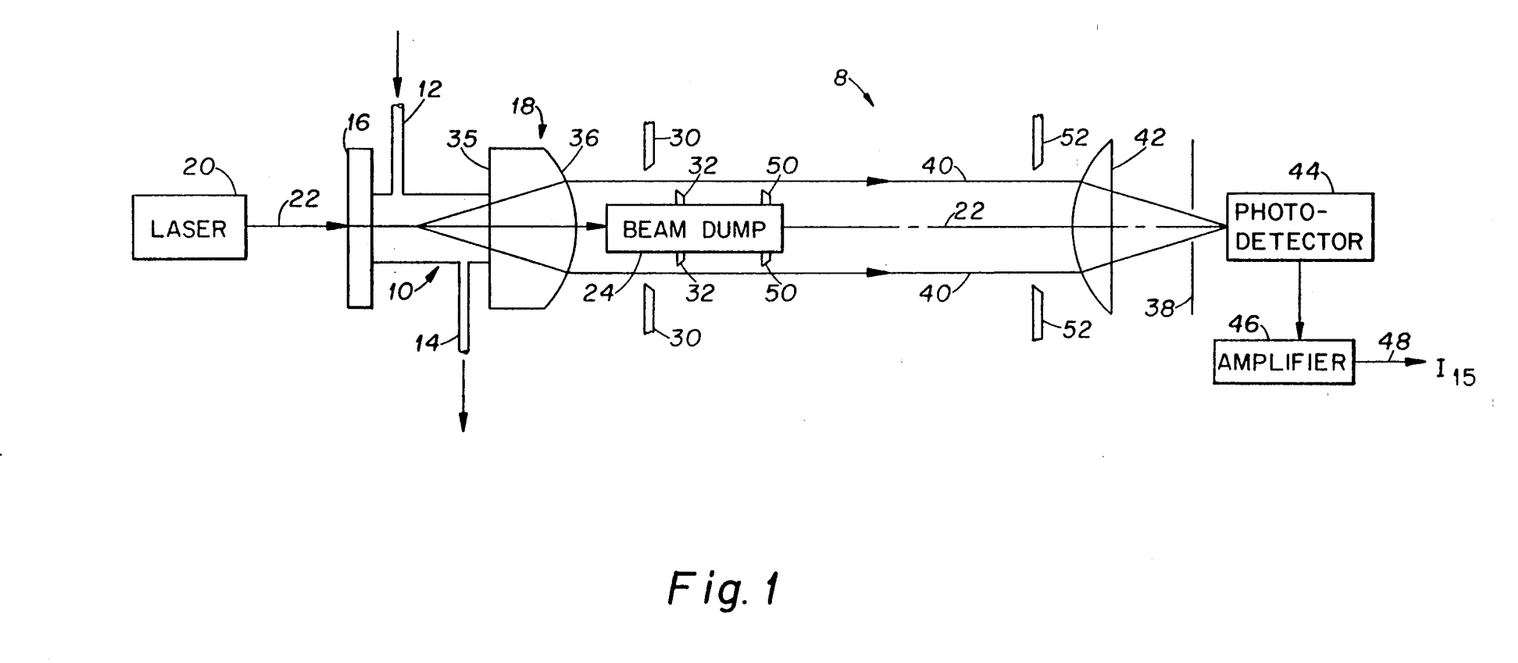
FIG. 1 is a schematic diagram of a molecular characterization detector in accordance with the present invention.

A schematic diagram of a molecular characterization detector 8 in accordance with the invention is shown in FIG. 1. A scattering cell 10 contains a sample for molecular characterization. The sample is in liquid form and flows continuously through scattering cell 10 from an inlet line 12 to an outlet line 14. The liquid sample is typically received from a liquid chromatography column. The liquid sample is typically a solvent containing a group of complex molecules having molecular weights in a range of about one thousand to one hundred million The scattering cell 10 includes a transparent window 16 at one end and a transparent window/lens 18 at the other end. The scattering cell 10 preferably has a small volume, on the order of about 10 microliters. In a preferred embodiment, scattering cell 10 has a length of about three millimeters and a diameter of about two millimeters.

A laser 20 directs a laser beam along an optical axis 22 through the scattering cell 10. The laser beam passes through window 16, through the liquid sample and through window/lens 18 and is intercepted by a beam dump 24. The beam dump 24 is constructed as described below to attenuate the light beam and to minimize reflections. The laser 20 typically has an output wavelength in the range of about 400 nanometers to 900 nanometers. The liquid sample must be substantially transparent to the laser wavelength. The laser beam that passes through scattering cell 10 is preferably polarized. In a preferred embodiment, the laser generates a polarized beam. The window 16 can have flat surfaces or can incorporate a lens for focusing the laser beam within the liquid sample. The laser beam is focused to its smallest diameter (a waist) at the center of the scattering cell 10 by laser optics, by an external lens that is preferably integral with window 16, or a combination thereof. In a preferred embodiment, the window 16 has flat surfaces.

The laser beam passing through scattering cell 10 is scattered by molecules of the liquid sample. As known in the art, the angular distribution of the scattered light depends on the properties of the molecules in the sample. The scattered light intensity at zero degrees, that is, in the direction of the laser beam along optical axis 22, can be used to determine the molecular weight of the molecules in the sample. However, the scattered light intensity at zero degrees is impractical to measure because the laser beam is many orders of magnitude more intense than the scattered light. It is common practice to measure the scattered intensity at a fixed angle relative to the optical axis 22. The light scattered at a predetermined angle is relatively low in intensity. Thus, light scattered by elements other than the molecules of the sample can interfere with the measurement. For example, light scattered by the surfaces of window 16 and window/lens 18 can potentially interfere with the measurement. Furthermore, since the laser beam is many orders of magnitude more intense than the scattered light, reflections of the laser beam from various elements in the system may reach the detector and interfere with the measurement.

The configuration of the molecular characterization detector shown in FIG. 1 substantially eliminates the stray scattered light and the stray reflected light and thus provides an extremely accurate measurement. It will be understood that the sample liquid in scattering cell 10 scatters the laser beam in different directions. The molecular characterization detector shown in FIG. 1 includes an arrangement of optical elements for selecting a measurement beam that comprises light from the laser beam that is scattered by the molecules of the sample in scattering cell 10 in a predetermined range of angles relative to optical axis 22. In a preferred embodiment, the detector selects light scattered by the sample molecules in a range of 14° to 16°.

Figures 3, 4:
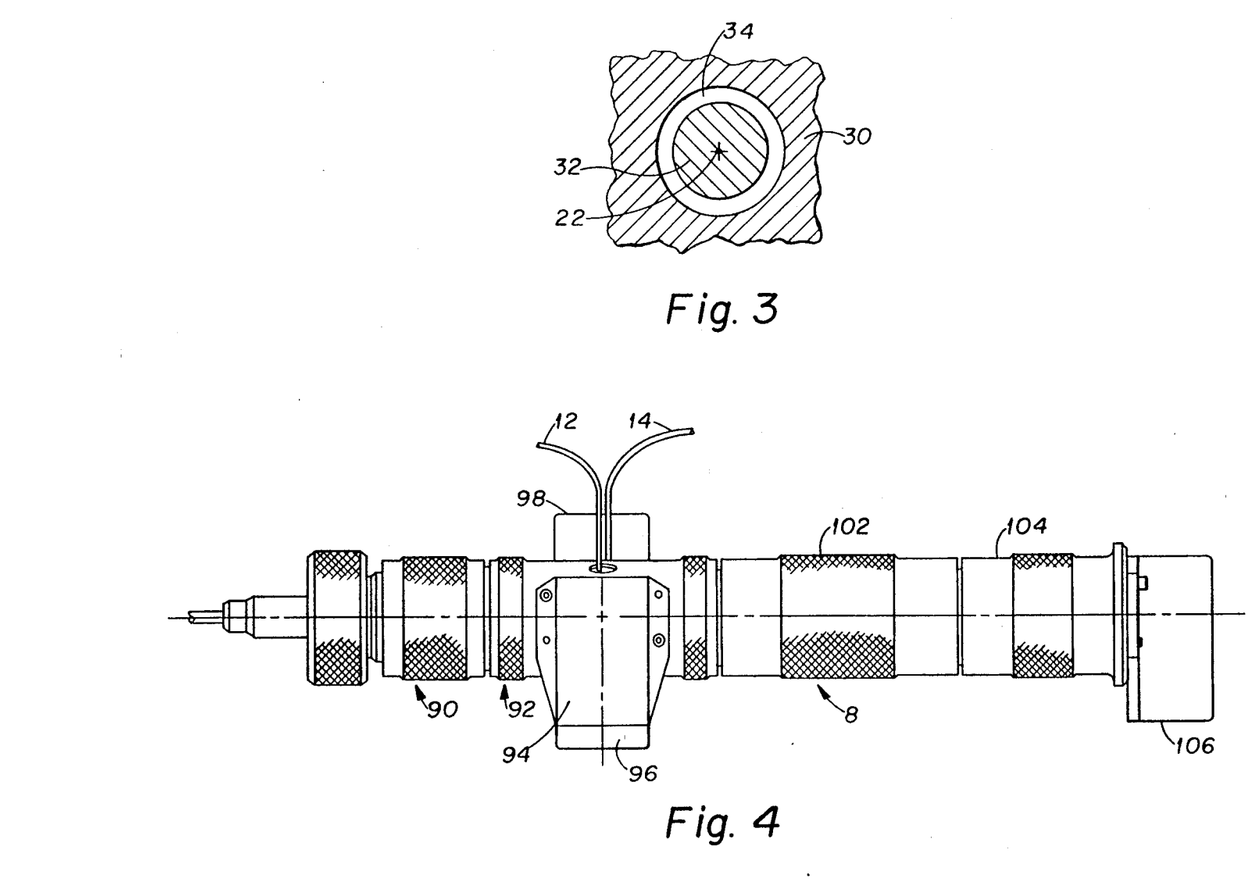
FIG. 3 is an axial view of the annular aperture used in the molecular characterization detector.
FIG. 4 is an outline drawing of the molecular characterization detector of the invention.

An iris 30 having a circular inside diameter centered on axis 22 and an iris 32 having a circular outside diameter centered on axis 22 define an annular aperture 34 (FIG. 3). The window/lens 18 at the output end of scattering cell 10 includes a flat surface 35 and an integral spherical surface 36 that functions as a lens to focus scattered light on annular aperture 34. The irises 30 and 32 are dimensioned to pass light scattered by the sample molecules in scattering cell 10 in a range of angles between 14° and 16°. Light scattered at angles less than 14° is blocked by iris 32, and light scattered at angles greater than 16° is blocked by iris 30. The design of the window/lens 18 and irises 30 and 32 is discussed in more detail below. A measurement beam 40 comprising scattered light in a predetermined range of angles relative to optical axis 22 that passes through annular aperture 34 is directed through a focusing lens 42 and an aperture 38 to a photodetector 44. The photodetector 44 senses the measurement beam 40 and provides an electrical signal. The electrical signal is amplified by an amplifier 46 to provide an output electrical signal $I_{15}$ representative of the intensity of the measurement beam.

As indicated above, light scattered by the surfaces of window 16 and window/lens 18 can potentially interfere with the measurement of light scattered by sample molecules. To avoid this problem, the molecular characterization detector of FIG. 1 includes optical elements for selecting scattered light from a predetermined portion of the scattering cell 10 and for blocking light that is scattered from other portions of the scattering cell 10. Preferably, scattered light from a central portion of scattering cell 10 along optical axis 22 is selected, thereby blocking light scattered by window 16 and window/lens 18. In a preferred embodiment, light from the center one third of the scattering cell 10 is selected. The selection of light scattered from the central portion of scattering cell 10 is performed by an iris 50 having a circular outside diameter centered on optical axis 22 and an iris 52 having a circular inside diameter centered on optical axis 22. The irises 50 and 52 function, as described in more detail below, in combination with window/lens 18 to select light scattered from the central portion of scattering cell 10.

Figure 2:
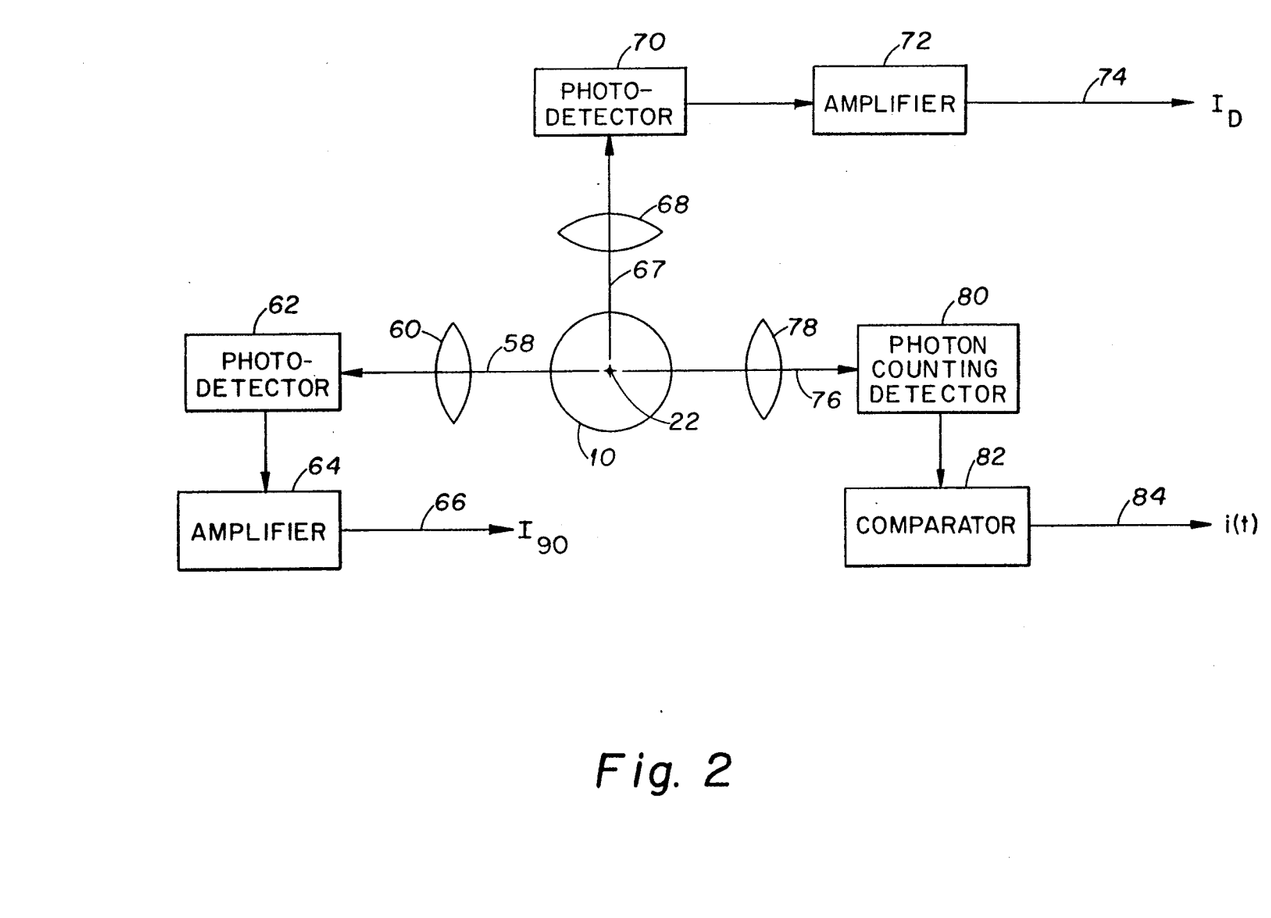
FIG. 2 is a cross section of the scattering cell of the molecular characterization detector showing detectors for detecting perpendicular scattering.

A cross-sectional view of the scattering cell 10 is shown in FIG. 2. The molecular characterization detector is provided with three additional detectors for detecting light scattered by the liquid sample in cell 10. The three additional detectors are omitted from FIG. 1 for ease of understanding. Light from the laser beam that is scattered by the sample molecules in a solid angle between about 0.1 and 1.0 steradian centered in a direction perpendicular to the laser beam and perpendicular to the direction of polarization of the laser beam defines a measurement beam 58 that passes through a focusing lens 60 to a photodetector 62. The output of photodetector 62 is amplified by an amplifier 64 to provide an electrical signal $I_{90}$ representative of measurement beam 58 on an output 66. Light from the laser beam that is scattered by the sample molecules in a solid angle of about $3 \times 10^{-4}$ steradian centered in a direction perpendicular to the laser beam and parallel to the direction of polarization of the laser beam defines a measurement beam 67 that passes through a focusing lens 68 to a photodetector 70. The output of photodetector 70 is amplified by an amplifier 72 to provide an electrical signal $I_D$ representative of measurement beam 67 on an output 74. A measurement beam 76 comprising fluctuations in light that is scattered by the sample molecules in a solid angle of about $10^{-4}$ steradian centered in a direction perpendicular to the laser beam passes through a focusing lens 78 to a photon counting detector 80. The output of photon counting detector 80 is converted to logic level pulses by a comparator 82 to provide an electrical signal i(t) representative of the measurement beam 76 on an output 84. Each pulse represents the detection of a single photon. Processing of the electrical signals $I_{90}$, $I_D$ and i(t) is described below.

An outline drawing of a molecular characterization detector in accordance with the present invention is shown in FIG. 4. A laser assembly 90 is connected to an input end of a sample cell and lens assembly 92. The assembly 92 contains scattering cell 10, window 16, window/lens 18 and the lens and detector elements shown in FIG. 2. Preferably, the wall of the scattering cell 10 is stainless steel, and the lenses 60, 68 and 78 are graded index lenses sealed into holes drilled in the scattering cell wall. This configuration minimizes the number of glass interfaces that can generate undesired stray light. The amplifiers 64 and 72 and comparator 82 are mounted in electronics assemblies 94, 96 and 98, respectively. An output end of assembly 92 is attached to the input end of an iris and beam dump assembly 102, which contains irises 30, 32, 50 and 52, and beam dump 24. The output end of assembly 102 is connected to a lens and detector assembly 104 having an electronics assembly 106 mounted thereon. The assembly 104 contains lens 42 and aperture 38. The photodetector 44 and amplifier 46 are contained within electronics assembly 106.

Figure 5:
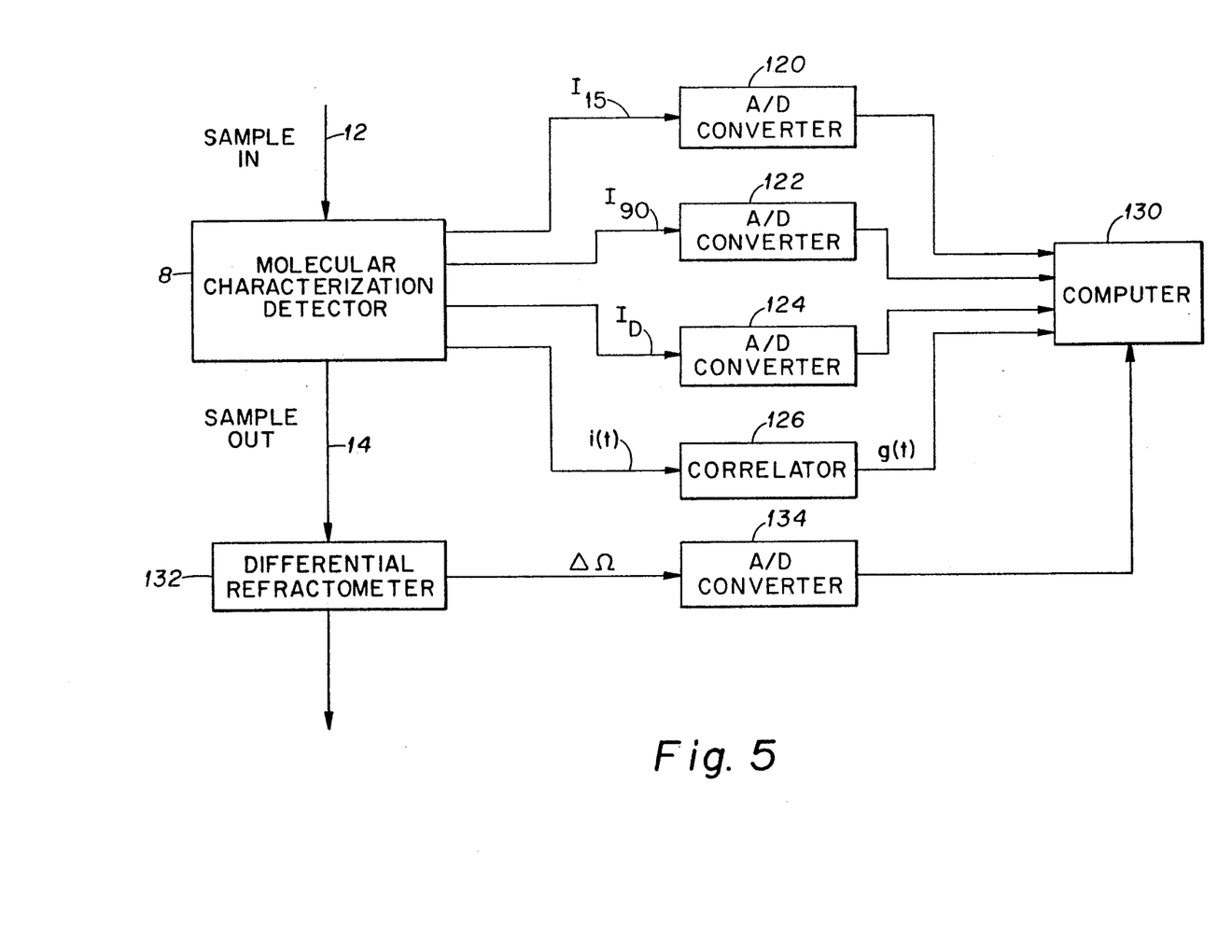
FIG. 5 is a block diagram of a molecular characterization instrument in accordance with the invention.

A block diagram of a molecular characterization instrument in accordance with the present invention is shown in FIG. 5. The molecular characterization detector 8 receives a liquid sample on inlet line 12 at a constant flow rate from a liquid chromatography column. The liquid sample is exhausted through outlet line 14. The output electrical signals $I_{15}$, $I_{90}$ and $I_D$ are coupled through analog-to-digital converters 120, 122 and 124, respectively, to a computer 130. The electrical signal $i(t)$ from comparator 84 is coupled to a correlator 126. An output $g(t)$ of correlator 126 is input to computer 130

The outlet line 14 from molecular characterization detector 8 is input to a differential refractometer 132. The differential refractometer 132 includes two sample cells divided by a diagonal window. One cell contains the liquid sample received through line 14, which includes molecules to be characterized. The other cell contains the liquid solvent without molecules to be characterized. A light beam is directed through the two cells and is refracted by the materials in the cells by a deviation angle $\Delta\Omega$. The output of the differential refractometer is an electrical signal that represents the deviation angle $\Delta\Omega$ of the sample. The output of the differential refractometer 132 is coupled through an analog to digital converter 134 to computer 130. In a preferred embodiment, the differential refractometer 132 is a Waters Model 410 Differential Refractometer. The computer 130 analyzes the signals $I_{15}$, $I_{90}$, $I_D$, $g(t)$ and $\Delta\Omega$ to provide a molecular characterization of the sample as described below. Although the molecular characterization detector 8 and the differential refractometer 132 are shown in FIG. 5 as separate units, they can be combined as a single unit.

Figure 6:
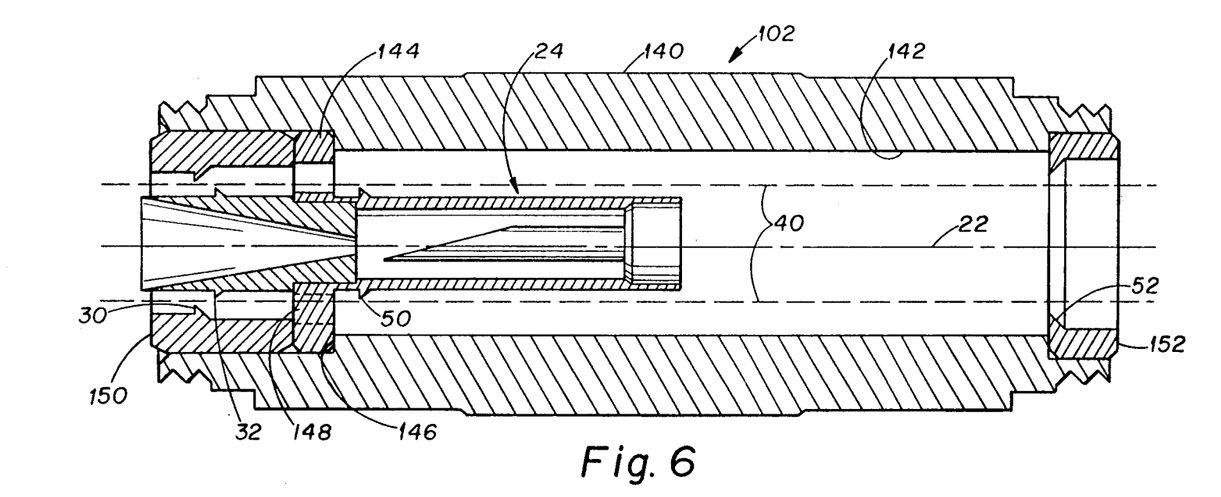
FIG. 6 is a cross-sectional view of the iris and beam dump assembly.

A cross-sectional view of a preferred embodiment of the iris and beam dump assembly 102 is shown in FIG. 6. The assembly includes a cylindrical housing 140 that is threaded at one end for attachment to scattering cell and lens assembly 92 and is threaded at the other end for attachment to lens and detector assembly 104. The housing 140 is provided with a generally cylindrical central bore 142 that is centered on optical axis 22. The bore 142 can be roughened, preferably by threading, to reduce reflections. The beam dump 24 is mounted within housing 140 and is centered on axis 22. The beam dump 24 includes an annular collar 144 that is positioned in abutment with a ridge 146 in bore 142. The annular collar 144 is provided with a plurality of radial spokes 148 that support beam dump 24. The dimensions of spokes 148 are minimized to permit passage of the measurement beam 40. The iris 30 is formed on an iris ring 150 mounted in housing 140 in abutment with annular collar 144. The iris 30 is formed as a tapered circular edge that is centered on axis 22. Iris 32 and iris 50 are formed on the external surface of beam dump 24. In each case, the iris is formed as a tapered circular edge having an outside diameter that is centered on optical axis 22. The iris 52 is formed on an iris ring 152 mounted in housing 140 at its output end. The iris 52 is formed as a tapered circular edge and has an inside diameter that is centered on optical axis 22. The beam dump 24 is described in detail below.

The operation of the molecular characterization detector in selecting measurement beam 40 will now be described. A scattering angle of 15° was selected. The principal difficulty in making light scattering intensity measurements is the elimination of stray light. This is easy to accomplish at a scattering angle of 90° but becomes more and more difficult as the angle is reduced toward 0° or 180°. However, the most accurate measurements of molecular weight of large molecules are obtained at a scattering angle of 0°, so it is desirable to make the measurement as close as possible to 0°. At larger angles, the molecular weight of large molecules is underestimated, although smaller molecules are measured accurately. At a scattering angle of 90°, molecular weights less than 45,000 can be measured to 1% accuracy. In order to measure the molecular weight of a material to 1% accuracy at one million Daltons, the scattering angle must be 17° or less. To meet this requirement, a scattering angle of 15° is used in the preferred embodiment of the invention. It will be understood that other scattering angles can be utilized, with an associated change in performance.

In order to provide sufficient signal strength, a range of scattering angles between 14° and 16° is utilized. All light scattered at angles outside the range of 14° to 16° is blocked by irises 30 and 32 from reaching the photodetector 44. Furthermore, as discussed above, it is desired to block light scattered by the window 16 and the window/lens 18 at opposite ends of scattering cell 10, even when the scattered light falls within the range of 14° to 16°. Since the laser beam has a finite diameter, it is necessary to block light scattered from a region at the ends of the cell having a diameter somewhat larger than the diameter of the laser beam. In the present example, light scattered from a region within 0.15 millimeter from axis 22 at the ends of the scattering cell 10 is blocked by irises 50 and 52 from reaching the photodetector 44.

For convenience, the window/lens 18 is designed such that a light ray scattered from the center of the cell 10 at an angle of 15° emerges from the window/lens 18 parallel to axis 22. In a preferred embodiment, the window/lens 18 has a thickness along axis 22 of about 30 millimeters, and surface 36 has a radius of curvature of 10.96 millimeters. The window/lens 18 has a diameter of about 20 millimeters and is fabricated of fused silica. As discussed above, the window/lens 18 is highly advantageous in the operation of the molecular characterization detector because the number of optical surfaces that can cause undesired scattering is minimized. It can be shown that all light scattered from optical axis 22 at a given angle crosses in a plane corresponding to the focal length of window/lens 18. The iris 30 is positioned in a plane in which light scattered at an angle of 16° is most nearly focused by window/lens 18. Similarly, the iris 32 is positioned in a plane in which light scattered at an angle of 14° is most nearly focused by window/lens 18. Due to spherical aberrations in window/lens 18, iris 30 is axially spaced from iris 32 in order to insure that each iris provides optimum blockage of scattered light outside the range of 14° to 16°. It can be shown that light scattered at 16.5° or more is intercepted by iris 30 and light scattered at 13.5° or less is intercepted by iris 32.

As discussed above, iris 50 and iris 52 pass light scattered from the center portion of cell 10 and block light scattered near the ends of cell 10 in the regions of window 16 and window/lens 18. The iris 50 is positioned in a plane in which light scattered from the input end of scattering cell 10 at angles between 14° and 16° is most nearly focused. The diameter of iris 50 is determined by performing ray traces originating at 0.15 millimeter off axis at the input end of the scattering cell and verifying that these rays will be blocked by iris 50. The iris 52 is positioned in a plane in which light scattered from the output end of the scattering cell 10 at angles between 14° and 16°. is most nearly focused. The diameter of iris 52 is determined by performing ray traces originating at 0.15 millimeter off axis at the output end of the cell and verifying that these rays are blocked by iris 52.

Figure 7:
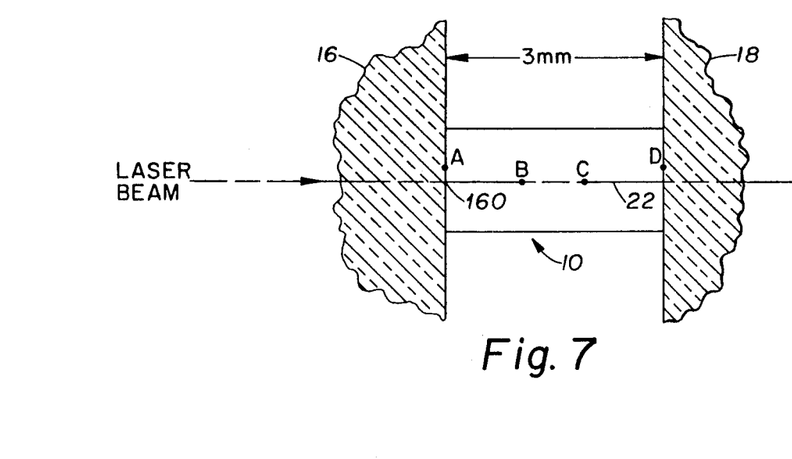
FIG. 7 is an enlarged schematic diagram of the scattering cell.

Ray traces illustrating the operation of irises 30, 32, 50 and 52 are shown in FIGS. 8-11. The ray traces shown in FIGS. 8 11 were made using a beam tracing program called Beam 3. The origins of the scattered rays shown in FIGS. 8-11 are illustrated in FIG. 7, which is a simplified schematic diagram of scattering cell 10. The origin of the coordinate system used in the ray diagrams is a point 160, as shown in FIG. 7, located on optical axis 22 at the input end of scattering cell 10 where the laser beam enters the liquid sample from window 16. The Z-axis coincides with optical axis 22, and the X axis is perpendicular to optical axis 22. It will be understood that the elements shown in the ray diagrams of FIGS. 8-11 are not drawn to scale.

Figure 8:
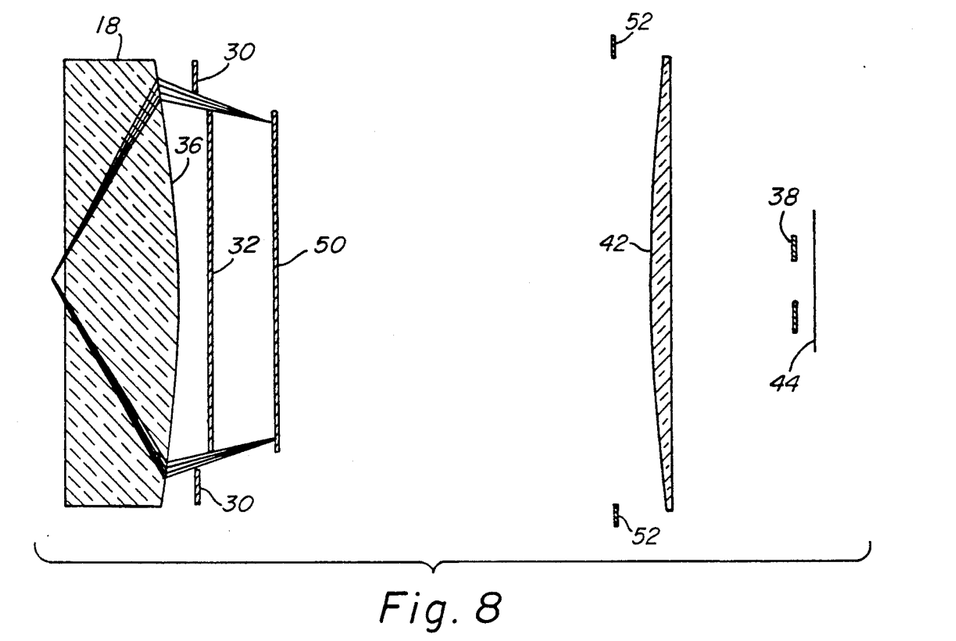
FIG. 8 is a ray diagram for the molecular characterization detector showing light scattered in a range of 14° to 16° from point A in FIG. 7.

The ray diagram of FIG. 8 shows the path of rays originating at point A (see FIG. 7) in the scattering cell and scattered at angles in the range of 14° to 16°. Point A is located at Z=0 and X=0.15 millimeter from axis 22. As shown in FIG. 8, all of the rays pass through the annular aperture defined by irises 30 and 32 (since they are within the range of 14° to 16°). However all rays originating at point A are intercepted by iris 50. This demonstrates that scattered light from the surface of window 16 does not reach photodetector 44.

Figure 9:
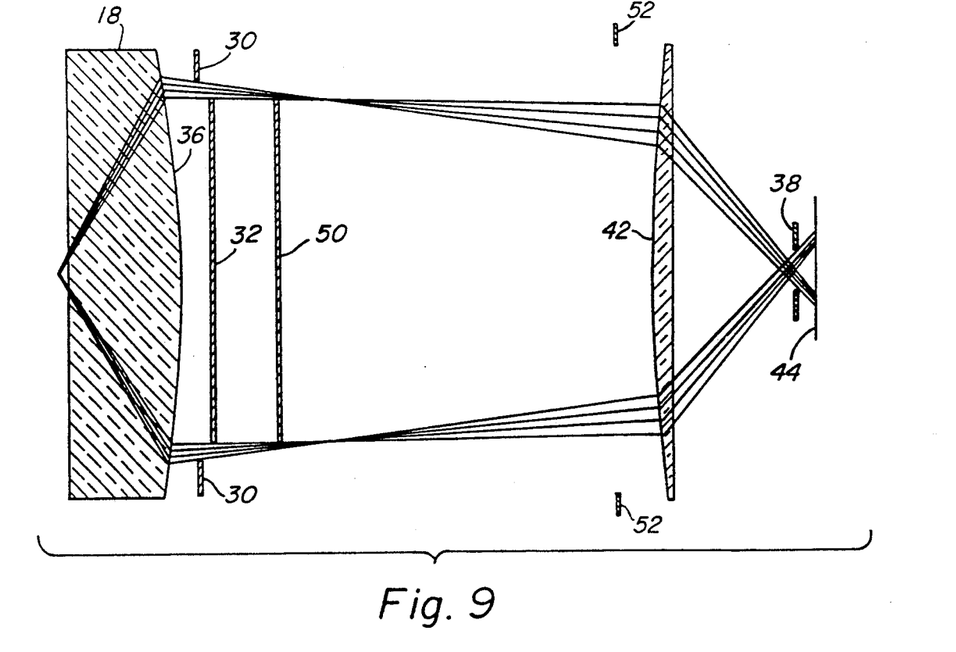
FIG. 9 is a ray diagram for the molecular characterization detector showing light scattered in a range of 14° to 16° from point B in FIG. 7.
Figure 10:
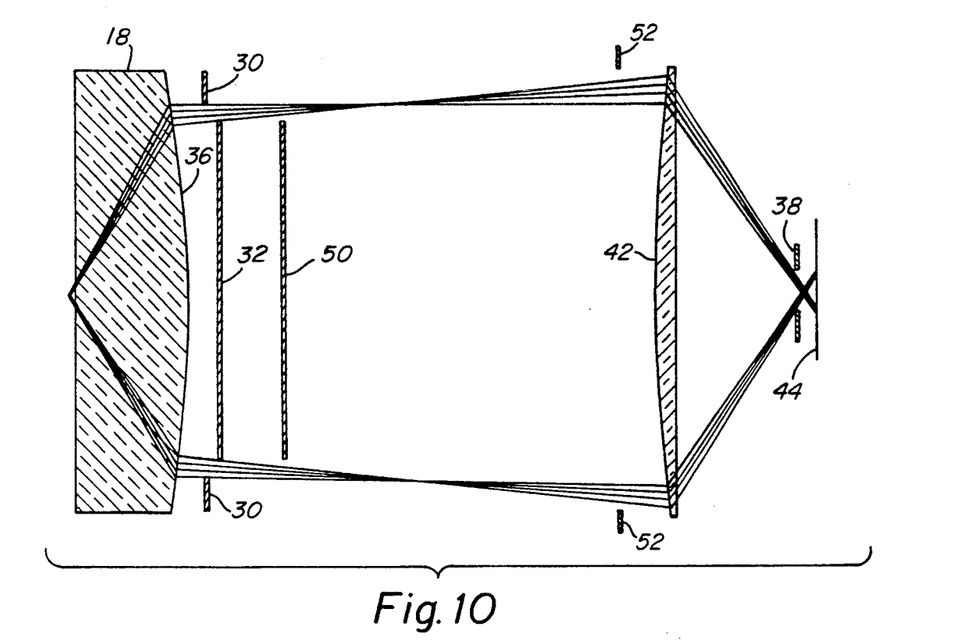
FIG. 10 is a ray diagram for the molecular characterization detector showing light scattered in a range of 14° to 16° from point C in FIG. 7.

FIG. 9 shows a ray diagram for rays originating at point B in the scattering cell and scattered at angles of 14° to 16°. The coordinates of point B Z=1.0 millimeter and X=0 (on axis 22). Similarly, a ray diagram for rays originating at point C in the scattering cell and scattered at angles of 14° to 16° is shown in FIG. 10. The coordinates of point C are Z=2.0 millimeters and X=0 (on axis 22). In FIGS. 9 and 10, all rays pass through the annular aperture defined by irises 30 and 32 and also pass through irises 50 and 52 and reach photodetector 44. The central region of the scattering cell on axis 22 between points B and C is the region from which the measurement beam is selected. In this region, light is scattered by molecules of the liquid sample rather than by window or lens surfaces.

Figure 11:
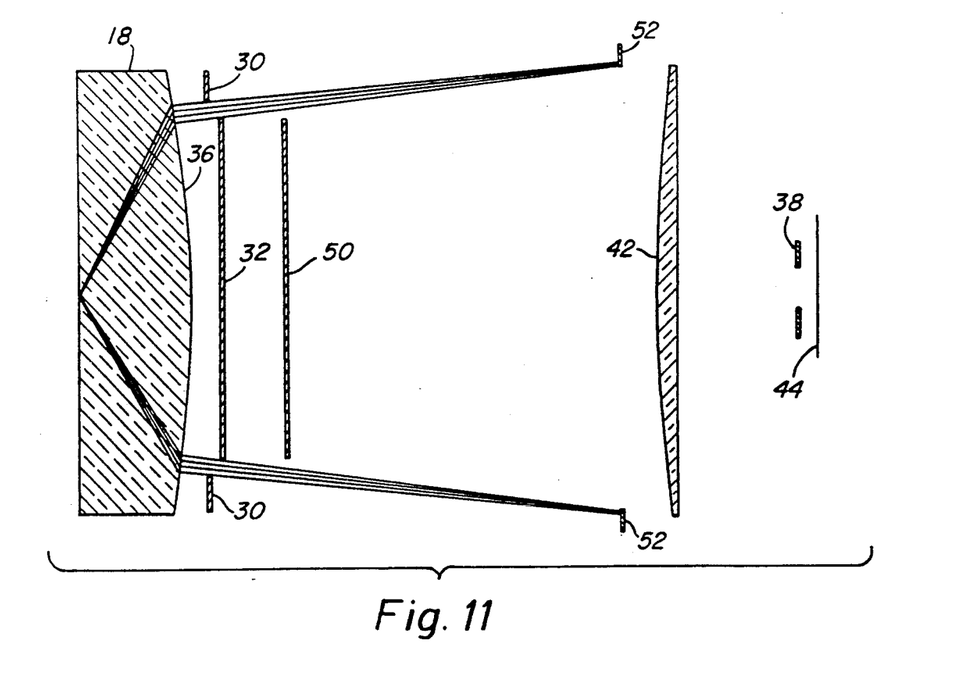
FIG. 11 is a ray diagram for the molecular characterization detector showing light scattered in a range of 14° to 16° from point D in FIG. 7.

A ray diagram for light originating from point D in scattering cell 10 and scattered at angles in the range of 14° to 16° is shown in FIG. 11. The coordinates of point D are Z=3.0 millimeters and X=0.15 millimeter. Since the length of scattering cell 10 along axis 22 is three millimeters, the point D is located on the surface of window/lens 18. As shown in FIG. 11, all rays pass through the annular aperture defined by irises 30 and 32. However, all rays are intercepted by iris 52. Thus, light scattered from the surface of window/lens 18 is blocked from reaching photodetector 44.

The parameters of an example of the molecular characterization detector of the present invention are shown in Table 1 below. The Z position is the distance along axis 22 from point 160, as shown in FIG. 7. Point 160 is a point on axis 22 where the laser beam enters the liquid sample from window 16. It will be understood that the parameters shown in Table 1 are given by way of example only and that a variety of other optical parameters can be utilized within the scope of the present invention.

TABLE 1

| Optical Element | Z Position (mm) | Diameter or Radius (mm) |
| --- | --- | --- |
| Window 16 | 0 | 6.5 diameter |
| Window/lens 18 (surface 35) | 3.0 | 6.5 diameter |
| Window/lens 18 (surface 36) | 31.5 | 20 diameter |
| Iris 30 | 37.35 | 7.63 (inside radius) |
| Iris 32 | 40.75 | 6.91 (outside radius) |
| Iris 50 | 57.85 | 6.93 (outside radius) |
| Iris 52 | 145.5 | 9.04 (inside radius) |
| Lens 42 (curved surface) | 155.0 | 22 diameter |
| Lens 42 (flat surface) | 160.3 | 22 diameter |
| Aperture 38 | 195.2 | 0.8 (inside radius) |

An important advantage of the detector design described above is that two separate functions are achieved with a single lens (window/lens 18). This eliminates multiple glass-to air interfaces, which are always a source of stray light. The two functions that are achieved with window/lens 18 and irises 30, 32, 50, 52 are to select rays at scattering angles between 14° and 16°, and to select rays scattered from the center portion of the cell and eliminate all light scattered from the end portions of the scattering cell. The function of selecting rays at scattering angles between 14° and 16° is performed by irises 30 and 32 in what is often called a Fourier lens arrangement. If there are no spherical aberrations, all light at a given angle to the lens axis and originating on the axis will pass through a ring at the focal point of the lens. Thus, light scattered from the axis of the lens at a given angle can be selected with an annular slit. The width of the slit determines the range of angles that is selected. Because of the strong spherical aberrations in the window/lens 18, the focal plane is curved so that the inside and outside edges of the annular slit are located at different axial distances from the lens. This accounts for the spacing between irises 30 and 32.

Also because of the spherical aberrations in the window/lens 18, all the light from the two ends of the cell is focused by the single window/lens 18 to two circles rather than two points. Irises 50 and 52 select light from the desired region at the center of the cell. A more complicated lens arrangement can be utilized to form an image of the scattering region in the cell. Masks can then be used to block light from the ends of the image from reaching the photodetector 44. However, the disadvantage of a more complex lens arrangement is that each lens surface adds scattered light and consequently reduces measurement accuracy.

The beam dump 24 is utilized for attenuating unwanted light after the laser beam has passed through the liquid sample in scattering cell 10. If the laser beam is not attenuated by many orders of magnitude, unwanted reflected light would cause the accuracy of the measurement to be reduced. The laser beam that passes through the sample unscattered is a major portion of the unwanted light and is of very high intensity compared with the light collected at the selected scattering angles. If not attenuated, the laser beam would be reflected back into the sample by any surface that it hits and would cause spurious signals (noise) at the selected scattering angles, thereby reducing the signal-to-noise ratio of the desired measurement and reducing the accuracy of the instrument.

The beam dump 24 is located on the axis 22 of the detector so as to intercept and attenuate the laser beam to a very low level. As a result, any reflected light is negligible in comparison with the light that is measured at the selected scattering angles. The beam dump 24 includes light-absorbing surfaces arranged such that the laser beam, after passing through the scattering cell 10, must go through many reflections from light absorbing surfaces prior to being reflected back into the sample. This attenuates the reflection to well below a level that would adversely affect the signal-to noise ratio of the signal at the selected scattering angles.

Figure 12:
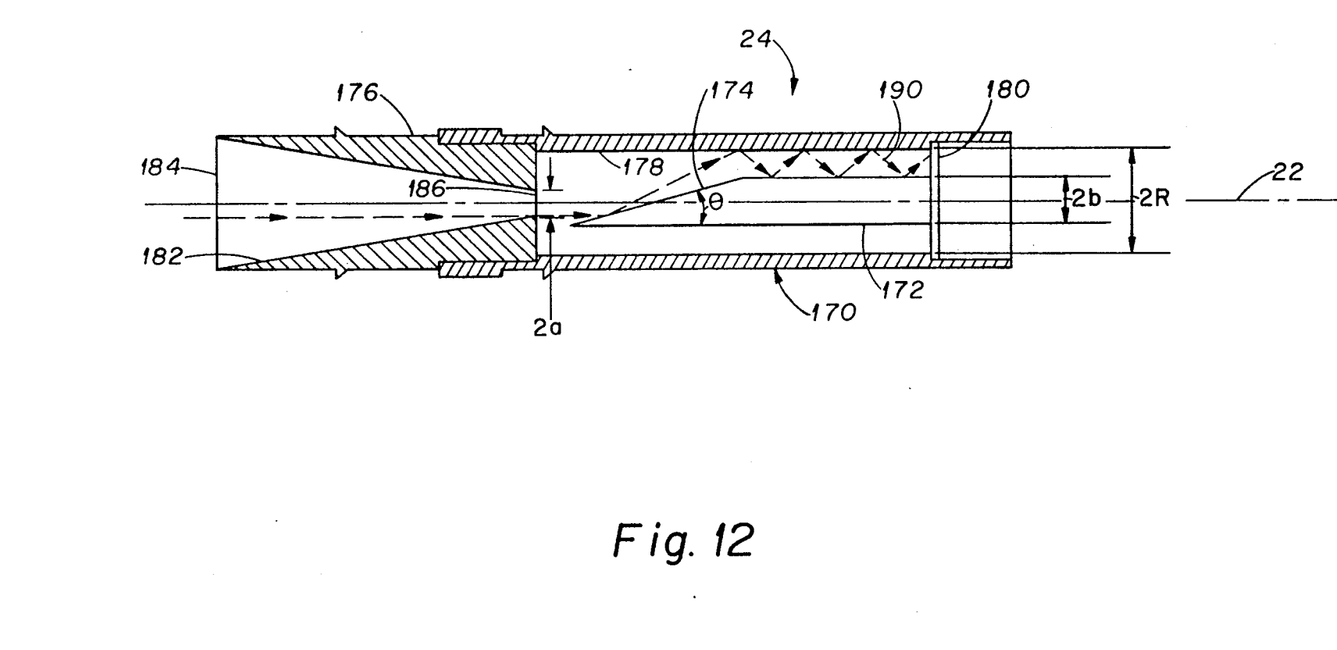
FIG. 12 is a cross sectional view of the beam dump.

A cross sectional view of the beam dump 24 is shown in FIG. 12. Beam dump 24 includes an enclosure 170, a post 172 having a light-absorbing surface 174 and a guide tube 176. The enclosure 170 includes a cylindrical wall having a light absorbing interior surface 178. The post 172 is axially positioned within enclosure 170 and has a circular cross section centered on optical axis 22. The light absorbing surface 174 is oriented at an angle $\theta$ with respect to optical axis 22. The post 172 is supported within enclosure 170 by a disk 180.

The guide tube 176 is mounted at the input end of enclosure 170 so as to guide the laser beam to light absorbing surface 174. The guide tube 176 has a truncated conical, light absorbing surface 182. A first opening 184 with a relatively large diameter receives the laser beam and a second opening 186 with a relatively small diameter defines an inlet to enclosure 170. The laser beam enters the beam dump 24 through the opening 184 in guide tube 176. The angle of the truncated conical, light absorbing surface 182 in guide tube 176 is selected such that all light entering the guide tube either passes directly into enclosure 170 through opening 186 or strikes the light-absorbing surface 182. Any light not absorbed by surface 182 is reflected through opening 186 into enclosure 170 or is reflected to surface 182 again. Ultimately, almost all the light entering the guide tube 176 passes through opening 186 into enclosure 170.

The interior surface 178 of enclosure 170 and the surface of post 172, including surface 174, are light absorbing. Preferably, the light absorbing surfaces are smooth, black anodized aluminum. The light entering enclosure 170 from guide tube 176 strikes light absorbing surface 174, and most of the incident light is absorbed. The light that is not absorbed is reflected to the interior wall 178 of enclosure 170 where further absorption occurs. Each reflection reduces the intensity of light substantially. The small fraction of light that can be reflected back through opening 186 is many orders of magnitude lower than the light that enters.

The post 172 and cylindrical wall of enclosure 170 define an annular space between them. The angle $\theta$ of light absorbing surface 174 relative to optical axis 22 is selected such that light entering enclosure through opening 186 and striking surface 174 is reflected several times in the annular space as indicated by the dashed line 190 in FIG. 12. In a preferred embodiment, the angle $\theta$ is 15°. In general, the dimension of light absorbing surface 174 must be sufficiently large to intercept any light entering enclosure 170 through opening 186. The angle $\theta$ is selected such that light reflected from surface 174 is reflected once from interior surface 178 and strikes the cylindrical portion of post 172. The diameter of opening 186 is selected to be substantially larger than the bright central portion of the laser beam. While the opening 186 is typically circular for receiving a round laser beam, opening 186 can be elliptical or rectangular in shape to receive laser beams that are noncircular. In a preferred embodiment, the inside radius of enclosure 170 is 0.1875 inch, the radius of post 172 is 0.075 inch and the radius of opening 186 is 0.0524 inch.

The beam dump 24 has been described as a part of the molecular characterization detector. It will be understood that the beam dump 24 shown and described above can be utilized in any application that requires attenuation of a light beam without substantial reflection.

The molecular characterization detector has been described above in connection with a liquid chromatography system. There are many alternative methods of preparing a sample for analysis by a detector, such as supercritical fluid chromatography, capillary electrophoresis, field flow fractionation and others. The molecular characterization detector of the present invention is not limited with respect to the method of preparation of the sample.

The measured values of the scattered light intensity $I_{15}$, $I_{90}$ and $I_D$, and the correlation function $g(t)$ are used by the computer 130 to calculate parameters for molecular characterization of the sample in scattering cell 10. The molecular weight $M_W$ and the radius of gyration $R_G$ are determined from:

$$M_W(dN/dC)\Delta\Omega = I_S(\theta)(K_{ins}(\theta)(1 + C(\theta)R^2_G)) \quad (1)$$

where dN/dC is the specific refractivity of the test sample, and $\Delta\Omega$ is the deviation angle measured in the differential refractometer. The measured intensity $I_S(\theta)$ at angle $\theta$ and is given by $$I_S(\theta) = I(\theta)_{solute} - I(\theta)_{solvent} \quad (2)$$

The value of $C(\theta)$ is given by $$C(\theta) = (16\pi^2 n^2_o / 3\lambda^2_o) \cdot \sin^2(\theta/2) \quad (3)$$

The value of dN/dC is known for a particular sample molecule/solvent system. The value of $K_{ins}(\theta)$, which is an instrumental constant, depends on the details of the optical collection system, the laser power and the laser wavelength. It can be determined empirically and is valid for all samples. Equation (1) thus contains two unknowns ($M_W$ and $R_G$). To solve for these values, the measured values of scattered light intensity $I_{15}$ and $I_{90}$ are substituted as the value of $I_S(\theta)$ to form two simultaneous equations. The simultaneous equations are solved to provide the values of molecular weight $M_W$ and radius of gyration $R_G$.

The hydrodynamic radius $R_h$ is determined from the measured correlation function which has the form:

$$g(t) = a + be^{-t/\tau} \quad (4)$$

where $1/\tau = 2DK^2$ is the exponential decay rate, $D = kT/6\pi\eta R_h$ is the diffusion constant and $K = (2\pi n_o/\lambda_o) \cdot \sin(\theta/2)$ is the scattering vector. In these expressions, k is Boltzman's constant, T is the temperature in Kelvin, $\eta$ is the solution viscosity, $R_h$ is the hydrodynamic radius and $\theta$ is the scattering angle. The value of $R_h$ can be determined by measuring $\tau$, since all other factors are known.

The shape factor of the sample molecules is defined in terms of eccentricity. A measure of the eccentricity e of a spheroid is given by:

$$e = ((A^2 - B^2)/A^2)^{\frac{1}{2}} \qquad (5)$$

where A and B are the axes of the spheroid. The eccentricity is determined from the polarization ratio $\rho_v$ defined as:

$$\rho_v = (I_D/I_{90}) \cdot (\alpha/\beta) \qquad (6)$$

where $\alpha$ is the solid angle for $I_{90}$ and $\beta$ is the solid angle for $I_D$. For a single measured value of $\rho_v$, two values of eccentricity may be calculated, one for a prolate spheroid and one for an oblate spheroid. A plot of polarization ratio $\rho_v$ as a function of eccentricity e is contained in the computer 130. For a given value of measured polarization ratio $\rho_v$, the eccentricity e is determined from the plot.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A molecular characterization detector comprising:
a scattering cell containing a sample or molecular characterization;
means for directing a light beam through said cell so that the light beam is scattered by said sample, said light beam defining an optical axis;
means for selecting from the scattered light a measurement beam comprising light from the light beam that is scattered by said sample from a predetermined portion of said scattering cell in a predetermined range of angles relative to said optical axis, said means for selecting a measurement beam comprising means including a first iris and a second iris for defining an annular aperture for passing said measurement beam, optical means for focusing light scattered by said sample on said annular aperture, a third iris having a circular outside diameter centered on said optical axis and a fourth iris having a circular inside diameter centered on said optical axis, said third iris and said fourth iris being located downstream of said annular aperture and being axially spaced apart, said third iris and said fourth iris selecting light that is scattered by said sample in a predetermined portion of said scattering cell; and
means for detecting said measurement beam and providing an output electrical signal representative of said measurement beam for characterization of said sample.

2. A molecular characterization detector as defined in claim 1 wherein said first iris blocks light scattered by said sample at angles greater than said predetermined range of angles and said second iris blocks light scattered by said sample at angles less than said predetermined range of angles.

3. A molecular characterization detector as defined in claim 2 wherein said first iris is located in a plane wherein light scattered by said sample at an upper limit of said predetermined range of angles is most nearly focused by said optical means.

4. A molecular characterization detector as defined in claim 3 wherein said second iris is located in a plane wherein light scattered by said sample at a lower limit of said predetermined range of angles is most nearly focused by said optical means.

5. A molecular characterization detector as defined in claim 4 wherein said first iris has a circular inside diameter centered on said optical axis and said second iris has a circular outside diameter centered on said optical axis.

6. A molecular characterization detector as defined in claim 4 wherein said optical means comprises a lens having a single spherical surface and wherein said first iris and said second iris are axially spaced apart on said optical axis.

7. A molecular characterization detector as defined in claim 6 wherein said scattering cell includes a window at an output end and wherein said lens is an integral part of said window.

8. A molecular characterization detector as defined in claim 2 wherein said optical means comprises a lens having a single spherical surface.

9. A molecular characterization detector as defined in claim 8 wherein said scattering cell includes a window at each end and wherein said third iris and said fourth iris block light from the light beam that is scattered by the window at each end of said scattering cell.

10. A molecular characterization detector as defined in claim 9 wherein said third iris and said fourth iris pass only the light from the light beam that is scattered by said sample in a central region of said scattering cell.

11. A molecular characterization detector as defined in claim 1 wherein said sample comprises a liquid and wherein the liquid is continuously circulated through said scattering cell.

12. A molecular characterization detector as defined in claim 1 wherein said light beam comprises a polarized laser beam.

13. A molecular characterization detector as defined in claim 1 wherein said predetermined range of angles is about 14° to 16°.

14. A molecular characterization detector as defined in claim 1 wherein said means for detecting said measurement beam comprises a photodetector and a lens for focusing said measurement beam on said photodetector.

15. A molecular characterization detector as defined in claim 1 further including a beam dump for attenuating said light beam after said light beam passes through said scattering cell.

16. A molecular characterization detector as defined in claim 15 wherein said beam dump comprises an enclosure having an inlet for receiving said light beam and a generally cylindrical light absorbing interior wall, and a surface located within said enclosure and positioned for intercepting said light beam, said surface being oriented to cause said light beam to undergo multiple reflections within said enclosure downstream of a point at which said surface intercepts said light beam and in a direction along said optical axis.

17. A molecular characterization detector as defined in claim 16 wherein said surface is formed on an axially positioned post within said enclosure, said post and the interior wall of said enclosure defining an annular space between them.

18. A molecular characterization detector as defined in claim 17 wherein the angle of said surface is selected to cause multiple reflections of said light beam in said annular space.

19. A molecular characterization detector as defined in claim 18 wherein said angle is about 15 degrees.

20. A molecular characterization detector as defined in claim 16 wherein said beam dump further includes means for guiding said light beam to the inlet of said enclosure.

21. A molecular characterization detector as defined in claim 20 wherein said means for guiding comprises a truncated conical, light-absorbing surface having a first opening that is larger than said inlet for receiving said light beam and a second opening that defines the inlet of said enclosure.

22. A beam dump for attenuating a light beam without substantial reflection, comprising:
   an enclosure having an inlet for receiving a light beam parallel to an optical axis and a light absorbing interior wall;
   a surface located within said enclosure and positioned for intercepting the light beam received through said inlet, said surface being oriented relative to said light beam at an angle selected to cause said light beam to undergo multiple reflections within said enclosure downstream of a point at which said surface intercepts said light beam and in a direction along said optical axis; and
   means for guiding said light beam to the inlet of said enclosure, said means for guiding comprising a truncated conical, light-absorbing surface having a first opening that is larger than said inlet for receiving said light beam and a second opening that defines the inlet of said enclosure.

23. A beam dump as defined in claim 22 wherein said truncated conical surface is selected to guide substantially all of said light beam through the inlet of said enclosure.

24. A molecular characterization instrument comprising:
   a scattering cell containing a sample for molecular characterization;
   means for directing a polarized light beam through said cell so that the light beam is scattered by said sample, said light beam defining an optical axis;
   means for detecting a first measurement beam comprising light from the light beam that is scattered by said sample in a predetermined range of angles relative to said optical axis and providing a first electrical signal representative of said first measurement beam for characterization of said sample;
   means for detecting a second measurement beam comprising light from the light beam that is scattered by said sample in a direction perpendicular to said light beam and perpendicular to a direction of polarization of said light beam and providing a second electrical signal representative of said second measurement beam for characterization of said sample;
   means for detecting a third measurement beam comprising light from the light beam that is scattered by said sample in a direction perpendicular to said light beam and parallel to the direction of polarization of said light beam and providing a third electrical signal representative of said third measurement beam for characterization of said sample;
   means for detecting a fourth measurement beam comprising fluctuations in light from the light beam that is scattered by said sample in a direction perpendicular to said light beam and providing a fourth electrical signal representative of said fourth measurement beam for characterization of said sample;
   means for determining the difference between the refractive index of the sample and a reference fluid by measuring a deviation angle of a light beam passing through a two chamber cell and providing a fifth electrical signal representative of said sample; and
   means for processing said first, second, third, fourth and fifth electrical signals to provide a molecular characterization of said sample.

25. A method for generating a signal for molecular characterization of a liquid sample comprising the steps of:
   directing a light beam through a scattering cell having a window at each end and containing a liquid sample for molecular characterization so that the light beam is scattered by the sample, the light beam defining an optical axis;
   selecting from the scattered light a measurement beam comprising light from the light beam that is scattered by the sample from a predetermined portion of the scattering cell in a predetermined range of angles relative to the optical axis, the step of selecting a measurement beam including the steps of selecting light within said predetermined range of angles with an annular aperture and blocking light from the light beam that is scattered by the window at each end of said scattering cell with axially spaced apart irises located downstream of said annular aperture; and
   detecting the measurement beam and providing an output electrical signal representative of the measurement beam for characterization of the sample.

26. A molecular characterization detector comprising:
   a scattering cell containing a sample for molecular characterization;
   means for directing a light beam through said cell so that the light beam is scattered by said sample, said light beam defining an optical axis;
   means for selecting from the scattered light a measurement beam comprising light from the light beam that is scattered by said sample in a predetermined range of angles relative to said optical axis, said means for selecting a measurement beam comprising means for defining an annular aperture for passing said measurement beam and optical means for focusing light scattered by said sample on said annular aperture, said means for defining an annular aperture comprising a first iris for blocking light scattered by said sample at angles greater than said predetermined range of angles and a second iris for blocking light scattered by said sample at angles less than said predetermined range of angles, said optical means comprising a lens having a single spherical surface, said first iris and said second iris being axially spaced apart on said optical axis; and
   means for detecting said measurement beam and providing an output electrical signal representative of said measurement beam for characterization of said sample.

* * * * *